(12) United States Patent
Periaki et al.

(10) Patent No.: US 10,881,301 B2
(45) Date of Patent: Jan. 5, 2021

(54) SPATIAL OPTIMIZATION FOR MEASURING BIOLOGICAL ANALYTES

(71) Applicant: BioSpex, Inc., San Jose, CA (US)

(72) Inventors: Clint Periaki, San Jose, CA (US); Wei Yang, Los Altos Hills, CA (US); Jiani Huang, San Jose, CA (US)

(73) Assignee: BioSpex, Inc., San Jose, CA (US)

( * ) Notice: Subject to any disclaimer, the term of this patent is extended or adjusted under 35 U.S.C. 154(b) by 30 days.

(21) Appl. No.: 16/405,968

(22) Filed: May 7, 2019

(65) Prior Publication Data

US 2020/0352444 A1    Nov. 12, 2020

(51) Int. Cl.
*A61B 5/00*    (2006.01)
*G01N 21/359*    (2014.01)

(52) U.S. Cl.
CPC ......... *A61B 5/0075* (2013.01); *G01N 21/359* (2013.01)

(58) Field of Classification Search
CPC .......................... A61B 5/0075; G01N 21/359
See application file for complete search history.

(56) References Cited

U.S. PATENT DOCUMENTS

| | | | |
|---|---|---|---|
| 5,615,673 A | 4/1997 | Berger et al. | |
| 6,665,556 B1 | 12/2003 | Alfano et al. | |
| 7,647,092 B2 * | 1/2010 | Motz | A61B 5/4312 600/478 |
| 8,072,595 B1 | 12/2011 | Bastiaans et al. | |
| 8,325,337 B2 | 12/2012 | Sinfield et al. | |
| 8,570,507 B1 | 10/2013 | Cooper et al. | |
| 8,873,041 B1 | 10/2014 | Chai et al. | |
| 10,548,481 B2 | 2/2020 | Yang et al. | |
| 10,760,969 B1 | 9/2020 | Wang et al. | |
| 2003/0059820 A1 | 3/2003 | Vo-Dinh | |
| 2007/0252978 A1 | 11/2007 | Van Der Voort et al. | |
| 2008/0129992 A1 | 6/2008 | Matousek et al. | |

(Continued)

OTHER PUBLICATIONS

Cooper, John B. et al., "Sequentially Shifted Excitation Raman Spectroscopy: Novel Algorithm and Instrumentation or Fluorescence-Free Raman Spectroscopy in Spectral Space", Society for Applied Spectroscopy, vol. 67, No. 8, 2013, pp. 973-984.

(Continued)

*Primary Examiner* — Mark R Gaworecki
(74) *Attorney, Agent, or Firm* — Carr & Ferrell LLP

(57) ABSTRACT

Systems and methods for spatial optimization of blood measurements in tissue are disclosed. Exemplary methods include: measuring a first Raman signal from the tissue with a probe at a first position; calculating a first percentage of a blood component in the first Raman signal; moving the probe a predetermined distance to a second position; measuring a second Raman signal with the probe at the second position; calculating a second percentage of the blood component in the second Raman signal; moving the probe the predetermined distance to a third position when the second percentage is greater than the first percentage; measuring a third Raman signal with the probe at the third position; calculating a third percentage of the blood component in the third Raman signal; moving the probe to the second position when the third percentage is less than the second percentage; and taking spectral measurements from the second position.

20 Claims, 9 Drawing Sheets

(56) References Cited

U.S. PATENT DOCUMENTS

| | | | |
|---|---|---|---|
| 2009/0105605 A1* | 4/2009 | Abreu | A61B 5/0046 |
| | | | 600/549 |
| 2011/0122407 A1 | 5/2011 | Jalali et al. | |
| 2012/0035442 A1 | 2/2012 | Barman et al. | |
| 2012/0287428 A1 | 11/2012 | Tamada | |
| 2013/0018237 A1* | 1/2013 | Henneberg | A61B 5/0068 |
| | | | 600/310 |
| 2015/0233836 A1* | 8/2015 | Okumura | A61B 5/1455 |
| | | | 436/501 |
| 2015/0342508 A1* | 12/2015 | Chong | A61B 5/0066 |
| | | | 600/301 |
| 2016/0354015 A1* | 12/2016 | Zhang | A61B 5/7225 |
| 2018/0164218 A1* | 6/2018 | Zavaleta | G01J 3/4412 |
| 2018/0310827 A1 | 11/2018 | Yang et al. | |
| 2018/0313692 A1 | 11/2018 | Yang et al. | |
| 2019/0015023 A1* | 1/2019 | Monfre | A61B 5/7203 |
| 2020/0124535 A1 | 4/2020 | Yang et al. | |
| 2020/0278255 A1 | 9/2020 | Wang et al. | |

OTHER PUBLICATIONS

Kostamovaara, J. et al., "Fluorescence suppression in Raman spectroscopy using a time-gated CMOS SPAD," Optics Express, Optics Society of America, vol. 21, No. 25, Dec. 13, 2013, 14 pages.

Nissinen, I. et al., "On the effects of the time gate position and width on the signal-to-noise ratio for detection of Raman spectrum in a time-gated CMOS single-photon avalanche diode based sensor," El Sevier, Sensors and Actuators B: Chemical, vol. 241, Mar. 31, 2017, pp. 1145-1152.

\* cited by examiner

SPATIAL OPTIMIZATION FOR MEASURING BIOLOGICAL ANALYTES

TECHNICAL FIELD

The present technology relates generally to spectral imaging, and more specifically to measurement of biological analytes.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

Spectroscopy (or spectrography) refers to techniques that employ radiation in order to obtain data on the structure and properties of matter. Spectroscopy involves measuring and interpreting spectra that arise from the interaction of electromagnetic radiation (e.g., a form of energy propagated in the form of electromagnetic waves) with matter. Spectroscopy is concerned with the absorption, emission, or scattering of electromagnetic radiation by atoms or molecules.

Spectroscopy can include shining a beam of electromagnetic radiation onto a desired sample in order to observe how it responds to such stimulus. The response can be recorded as a function of radiation wavelength, and a plot of such responses can represent a spectrum. The energy of light (e.g., from low-energy radio waves to high-energy gamma-rays) can result in producing a spectrum.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

The present disclosure is related to various systems and methods for spatial optimization for measuring biological analytes. Specifically, a method for spatial optimization of blood measurements in tissue may comprise: measuring a first Raman signal from the tissue with a probe at a first position; calculating a first percentage of a blood component in the first Raman signal; moving the probe a predetermined distance to a second position; measuring a second Raman signal from the tissue with the probe at the second position; calculating a second percentage of the blood component in the second Raman signal; moving the probe the predetermined distance to a third position when the second percentage is greater than the first percentage; measuring a third Raman signal from the tissue with the probe at the third position; calculating a third percentage of the blood component in the third Raman signal; moving the probe to the second position when the third percentage is less than the second percentage; and taking spectral measurements from the second position.

BRIEF DESCRIPTION OF THE DRAWINGS

Embodiments are illustrated by way of example, and not by limitation, in the figures of the accompanying drawings, in which like references indicate similar elements and in which.

DETAILED DESCRIPTION

Figure 1:
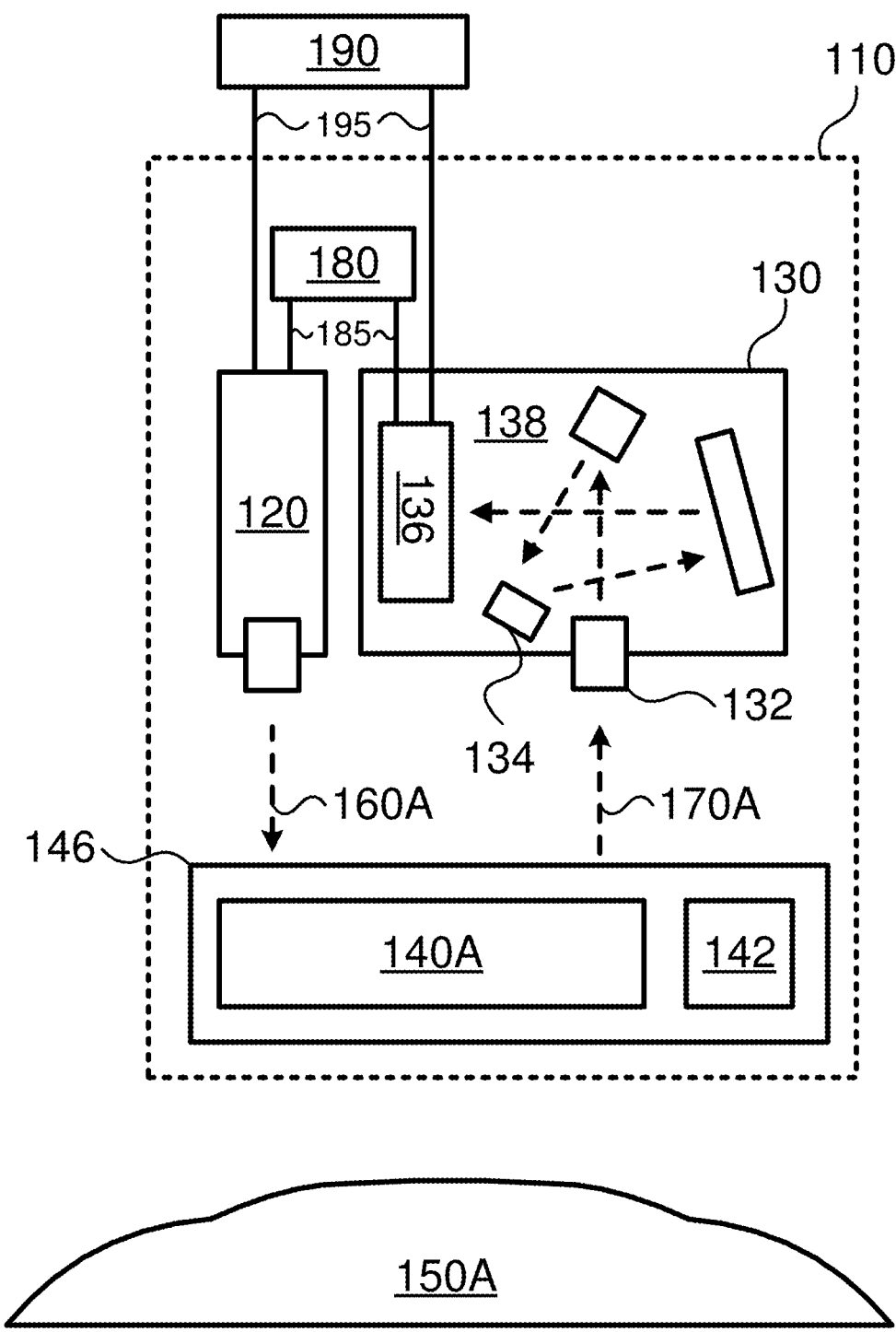
FIG. 1 is a simplified representation of a system for spatial optimization for measuring biological analytes, according to some embodiments.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated. The terminology used herein is for the purpose of describing particular embodiments only and is not intended to be limiting of the technology. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

FIG. 1 illustrates system 100 for spatial optimization of biological analyte measurements according to some embodiments. System 100 can include spectrometer 110, analyte 150A, and computing system 190.

According to some embodiments, analyte 150 is at least one of solid, liquid, plant tissue, human tissue, and animal tissue. For example, animal tissue is one or more of epithelial, nerve, connective, muscle, and vascular tissues. By way of further non-limiting example, plant tissue is one or more of meristematic (e.g., apical meristem and cambium), protective (e.g., epidermis and cork), fundamental (e.g., parenchyma, collenchyma and sclerenchyma), and vascular (e.g., xylem and phloem) tissues.

According to some embodiments, spectrometer 110 comprises excitation light source 120, optical bench 130, sampling apparatus 140A, stepper motor 142, and delay 180. Excitation light source 120 is a monochromatic light source, such as a laser, in accordance with some embodiments. For example, excitation light source 120 is at least one of an Nd:YAG (neodymium-doped yttrium aluminum garnet; Nd:Y3Al5O12), Argon-ion, He—Ne, and diode laser. By way of further non-limiting example, excitation light source 120 can provide light (electromagnetic waves) in a range between ultra-violet (UV) light (e.g., electromagnetic radiation with a wavelength from 10 nm to 400 nm) and short-wave near-infrared (NIR) (1.4 µm to 3 µm), including portions of the electromagnetic spectrum in-between, such as visible light (e.g., 380 nm-760 nm) and NIR light (e.g., 0.75 µm to 1.4 µm).

In various embodiments, excitation light source 120 is tunable—a wavelength of the light from excitation light source 120 is changed by one or more (predetermined) increments and/or to one or more (predetermined) values—such as by using heat control (e.g., from a heating element), electrical control (e.g., using microelectromechanical systems (MEMS)), and mechanical control (e.g., using a mechanism to turn a mirror). Preferably, excitation light source 120 provides high spectral purity, high wavelength stability, and/or high power stability output.

Sampling apparatus 140A performs various combinations and permutations of directing light 160 from excitation light source 120, collecting the resulting Raman scattered light or Raman scatter (among others) 170, filtering out radiation at the wavelength corresponding to the laser line (e.g., Rayleigh scattering), and providing the Raman scatter (among others) 170 to optical bench 130, according to some embodiments. For example, sampling apparatus 140A includes a microscope and/or an optical probe. By way of further non-limiting example, sampling apparatus 140A includes optical fiber, one or more filters (e.g., notch filter, edge-pass filter, and band-pass filter), and the like. Raman scatter (among others) 170 includes, for example, at least one of Raman scatter, fluorescence, and Rayleigh scattering (which can be filtered out by sampling apparatus 140A).

Sampling apparatus 140A can be attached to or mounted on translation stage (or linear stage) 146. Translation stage 146 can restrict the motion of sampling apparatus 140A to a single axis of motion (or one degree of freedom out of six degrees of freedom). In various embodiments, translation stage 146 can include a (moving) platform and a (fixed) base (not depicted in FIG. 1), where the platform moves relative to the base. The platform and base can be joined by some form of guide which restricts motion of the platform to only one dimension. For example, guide types can be rollers, recirculating ball bearing, flexure, cylindrical sleeve, dovetail, and the like.

The position of the (moving) platform relative to the (fixed) base is typically controlled by a linear actuator. For example, a lead screw can pass through a lead nut in the platform. Rotation of the lead screw can be controlled by a motor, such as stepper motor 142. In this way, translation stage 146 can move sampling apparatus 140A (e.g., a probe) in spatial relationship to analyte 150A in a controlled manner.

Stepper motor 142 can move translation stage 146 to precisely change the distance between sampling apparatus 140A and analyte 150A in steps (increments) ranging from 2 µm to 0.5 nm. Stepper motor 142 can be a brushless DC electric motor that divides a full rotation into a number of equal steps. Stepper motor 142's rotational position can then be controlled (e.g., by computing system 190) to move and hold at one of these steps without needing a position sensor for feedback. Although translation stage 146 is shown including sampling apparatus 140A and stepper motor 142, in various embodiments translation stage 146 can include other constituent parts of spectrometer 110 and computing system 190.

In accordance with some embodiments, optical bench 130 is a spectrograph. For example, optical bench 130 includes slit 132, spectral dispersion element 134, and detector 136. By way of non-limiting example, optical bench 130 measures wavelengths in one or more of the UV spectrum (10 nm to 400 nm), visible spectrum (e.g., 380 nm-760 nm), visible to near-infrared (e.g., 400 nm-1000 nm), short-wave infrared (e.g., 950 nm-1700 nm), and infrared (e.g., 1 µm-5 µm).

Slit 132, spectral dispersion element 134, and detector 136 can be arranged in optical bench 138, along with other components (e.g., monochromator—which transmits a mechanically selectable narrow band of wavelengths of light or other radiation chosen from a wider range of wavelengths available at an input—including one or more of a mirror, prism, collimator, holographic grating, diffraction grating, blazed grating, and the like), according to different configurations. For example, different configurations include: crossed Czerny-Turner, unfolded Czerny-Turner, transmission, and concave holographic optical benches.

Slit 132 can determine the amount of light (e.g., photon flux, such as Raman scatter (among others) 170) that enters optical bench 138. Dimensions (e.g., height and width, not shown in FIG. 1) of slit 132 can determine the spectral resolution of optical bench 130. By way of non-limiting example, a height of slit 132 can range from 1 mm to 20 mm. By way of further non-limiting example, a width of slit 132 can range from 5 µm to 800 µm.

Spectral dispersion element 134 can determine a wavelength range of optical bench 130 and can partially determine an optical resolution of optical bench 130. For example, spectral dispersion element 134 is a ruled diffraction grating or a holographic diffraction grating, in the form of a reflective or transmission package. Spectral dispersion element 134 can include a groove frequency and a blaze angle.

Detector 136 receives light and measures the intensity of scattered light. Detector 136 can be a one- or two-dimensional detector array comprised of a semiconductor material such as silicon (Si) and indium gallium arsenide (InGaAs). In some embodiments, a bandgap energy of the semiconductor determines an upper wavelength limit of detector 136. An array of detector 136 can be in different configurations, such as charged coupled devices (CCDs), back-thinned charge coupled devices (BT-CCDs), complementary metal-oxide-semiconductor (CMOS) devices, and photodiode arrays (PDAs). CCDs can be one or more of intensified CCDs (ICCDs) with photocathodes, back illuminated CCDs, and CCDs with light enhancing coatings (e.g., Lumogen® from BASF®). Detector 136 has a resolution of 8-15 wavenumbers, according to some embodiments. Detector 136 can be used to detect concentrations of molecules in a range of 1-1,000 mg per deciliter (mg/dL).

By way of further non-limiting example, detector 136 is a single pixel time-gated detector such as single-photon avalanche diode (SPAD), micro-channel plate (MCP), photomultiplier tube (PMT), silicon photomultiplier (SiPM), or avalanche photodiode (APD) that sits on a scanning motor driven rail, or detector arrays such as a single-photon avalanche diode (SPAD) array, or an intensified CCD (ICCD). A SPAD is a solid-state photodetector in which a photon-generated carrier (via the internal photoelectric effect) can trigger a short-duration but relatively large avalanche current. The leading edge of the avalanche pulse marks the arrival (time) of the detected photon. The avalanche current can continue until the avalanche is quenched (e.g., by lowering a bias voltage down to a breakdown voltage). According to various embodiments, each pixel in some SPAD arrays can count a single photon and the SPAD array can provide a digital output (e.g., a 1 or 0 to denote the presence or absence of a photon for each pixel).

To detect another photon, a control circuit(s) (not depicted in FIG. 1) integrated in and/or external to the SPAD can be used to read out measurements and quench the SPAD. For example, the control circuit can sense the leading edge of the avalanche current, generate a (standard) output pulse synchronous with the avalanche build up, quench the avalanche, and restore the diode to an operative level. The control circuit can provide passive quenching (e.g., passive quenching passive reset (PQPR), passive quench active reset (PQAR), and the like) and/or active quenching (e.g., active quench active reset (AQAR), active quenching passive reset (AQPR), and the like). In various embodiments, detector 136A is a complementary metal-oxide semiconductor (CMOS) SPAD array.

A micro-channel plate (MCP) is a planar component used for detection of single particles, such as photons. An MCP can intensify photons by the multiplication of electrons via secondary emission. Since a microchannel plate detector has many separate channels, it can also provide spatial resolution.

A photomultiplier tube (PMT) is a photoemissive device which can detect weak light signals. In a PMT, absorption of a photon results in the emission of an electron, where the electrons generated by a photocathode exposed to a photon flux are amplified. A PMT can acquire light through a glass or quartz window that covers a photosensitive surface, called a photocathode, which then releases electrons that are multiplied by electrodes known as metal channel dynodes. At the end of the dynode chain is an anode or collection electrode. Over a very large range, the current flowing from the anode to ground is directly proportional to the photoelectron flux generated by the photocathode.

Silicon photomultipliers (SiPM) are solid-state single-photon-sensitive devices based on Single-photon avalanche diode (SPAD) implemented on a common silicon substrate. Each SPAD in an SiPM can be coupled with the others by a metal or polysilicon quenching resistor.

Avalanche photodiodes (APDs) are semiconductor photodiodes with an internal gain mechanism. In an APD, absorption of incident photons creates electron-hole pairs. A high reverse bias voltage creates a strong internal electric field, which accelerates the electrons through the semiconductor crystal lattice and produces secondary electrons by impact ionization. The resulting electron avalanche can produce gain factors up to several hundred.

An intensified charge-coupled device (ICCD) is a CCD that is optically connected to an image intensifier that is mounted in front of the CCD. An image intensifier can include three functional elements: a photocathode, a micro-channel plate (MCP) and a phosphor screen. These three elements can be mounted one close behind the other. The photons which are coming from the light source fall onto the photocathode, thereby generating photoelectrons. The photoelectrons are accelerated towards the MCP by an electrical control voltage, applied between photocathode and MCP. The electrons are multiplied inside of the MCP and thereafter accelerated towards the phosphor screen. The phosphor screen converts the multiplied electrons back to photons which are guided to the CCD by a fiber optic or a lens. An image intensifier inherently includes shutter functionality.

For example, when the control voltage between the photocathode and the MCP is reversed, the emitted photoelectrons are not accelerated towards the MCP but return to the photocathode. In this way, no electrons are multiplied and emitted by the MCP, no electrons are going to the phosphor screen, and no light is emitted from the image intensifier. In this case no light falls onto the CCD, which means that the shutter is closed.

Detector 136 can be other photodetectors having a time resolution of about one nanosecond or less. By way of further non-limiting example, detector 136 is a streak camera array, which can have a time-resolution of around 180 femtoseconds. A streak camera measures the variation in a pulse of light's intensity with time. A streak camera can transform the time variations of a light pulse into a spatial profile on a detector, by causing a time-varying deflection of the light across the width of the detector.

A spectral resolution of a spectrum measured by detector 136 can depend on the number of pixels (e.g., discrete photodetectors) in detector 136. A greater number of pixels can provide a higher spectral resolution. Detector 136 can comprise a one-dimensional and/or two-dimensional array of pixels. For example, detector 136 has in a range of 32 to 1,048,576 pixels. According to some embodiments, detector 136 has in a range of 512 to 1,024 pixels.

In some embodiments, the output (e.g., measurements) from detector 136 is provided to an analog-to-digital converter (ADC) (not shown in FIG. 1). The ADC can be integrated into detector 136 or separate from detector 136, such as in at least one of optical bench 130, spectrometer 110, and computing system 190. The ADC can convert the measurements before the next measurements are received. For example, when measurements are received at 20 KHz, the ADC can convert at 20 KHz or faster. When the output of detector 136 is already a digital spectra, analog-to-digital conversion is not needed.

Spectrometer 110 can provide information about molecular vibrations to identify and quantify characteristics (e.g., molecules) of analyte 150. Spectrometer 110 can direct light (electromagnetic waves) 160 from excitation light source 120 (optionally through sampling apparatus 140A) onto analyte 150. Light 160 from excitation light source 120 can be said to be shone on analyte 150 and/or analyte 150 can be said to be illuminated by excitation light source 120 and/or light 160. When (incident) light from excitation light source 120 hits analyte 150, the (incident) light scatters. A majority (e.g., 99.999999%) of the scattered light is the same frequency as the light from excitation light source 120 (e.g., Rayleigh or elastic scattering).

A small amount of the scattered light (e.g., on the order of $10^{-6}$ to $10^{-8}$ of the intensity of the (incident) light from excitation light source 120) is shifted in energy from the frequency of light 160 from excitation light source 120. The shift is due to interactions between (incident) light 160 from excitation light source 120 and the vibrational energy levels of molecules in analyte 150. (Incident) Light 160 interacts with molecular vibrations, phonons, or other excitations in analyte 150, causing the energy of the photons (of light 160 from excitation light source 120) to shift up or down (e.g., Raman or inelastic scattering). The shift in energy (e.g., of Raman scatter 170 from analyte 150) can be used to identify and quantify characteristics (e.g., molecules) of analyte 150.

Optical bench 130 detects (an intensity of) the Raman scatter 170 using detector 136 (optionally received through sampling apparatus 140A).

Spectrometer 110 can further include delay 180 for gating, according to some embodiments. Delay 180 can be communicatively coupled to excitation light source 120 and detector 136 through communications 185. In various embodiments, delay 180 can detect when excitation light source 120 provides light 160 (e.g., a laser pulse is emitted). For example, delay 180 can have a sensor (not depicted in FIG. 1) which detects light 160 being emitted from excitation light source 120. By way of further non-limiting example, excitation light source 120 can provide a (electronic) signal to delay 180 when excitation light source 120 provides light 160 (e.g., fires laser pulse). A predetermined amount of time after light 160 is detected/signaled, delay 180 can provide a signal indicating to detector 136 to (effectively) stop detecting and provide measurements (e.g., report a photon count at that time). The predetermined amount of time can be a gate. For example, the predetermined amount of time (e.g., gate or time window) can be selected using the duration of light 160 (e.g., a laser pulse), characteristics of the analyte being measured (e.g., duration/lifetime of fluorescence), and the like.

Delay 180 can be an (programmable) analog (e.g., continuous time) and/or digital (e.g., discrete time) delay line. In some embodiments, delay 180 is a network of electrical components connected in series, where each individual element creates a time difference between its input signal and its output signal. In various embodiments, delay 180 comprises one or more delay elements (e.g., forming a (circular) buffer) such as in discrete logic (e.g., flip flops, inverters, digital (or voltage) buffer, and the like), (general purpose) microprocessor, digital signal processor, application specific standard product (ASSP), application-specific integrated circuit (ASIC), field-programmable gate array (FPGA), and the like. Although depicted as a part of spectrometer 110, delay 180 can alternatively be external to spectrometer 110, such as part of computing system 190.

Spectrometer 110 can be communicatively coupled to computing system 190 through communications 195. Communications 195 can be various combinations and permutations of wired and wireless communications (e.g., networks) described below in relation to FIG. 9. Computing system 190 can include a database of Raman spectra associated with known molecules and/or remotely access the database over a communications network (not shown in FIG. 1). In some embodiments, computing system receives intensity measurements from spectrometer 110, produces at least one Raman spectrum using data (e.g., intensity measurements) from spectrometer 110, and identifies and/or quantifies molecules in analyte 150 using the at least one Raman spectrum and a database of Raman spectra associated with known molecules.

In some embodiments, computing system 190 is a single computing device. For example, computing system 190 is a desktop or notebook computer communicatively coupled to Spectrometer 110 through a Universal Serial Bus (USB) connection, a WiFi connection, and the like. In various embodiments, computing system 190 can be various combinations and permutations of stand-alone computers (e.g., smart phone, phablet, tablet computer, notebook computer, desktop computer, etc.) and resources in a cloud-based computing environment. For example, computing system 190 is a smart phone and a cloud-based computing system. The smart phone can receive data (e.g., intensity measurements) from spectrometer 110 using USB, WiFi, Bluetooth, and the like. The smart phone can optionally produce at least one Raman spectrum using the data. The smart phone can transmit the data and/or at least one Raman spectrum to a cloud-based computing system over the Internet using a wireless network (e.g., cellular network). The cloud-based computing system can produce at least one Raman spectrum using the data and/or quantify and/or identify molecules in analyte 150 using the recovered Raman spectrograph. Although depicted as outside of spectrometer 110, additionally or alternatively at least part of computer system 190 can be integrated into spectrometer 110. Computing system 190 is described further in relation to FIG. 9.

According to some embodiments, spectrometer 110 offers at least some of the advantages of: differentiating chemical structures (even if they contain the same atoms in different arrangements), physical contact with analyte 150 not required, no damage to analyte 150 (e.g., non-destructive testing), preparation of analyte 150 is not required, analyte 150 can be in a transparent container (e.g., when light 160 is in the visible or near-visible light spectrum), sensitivity to small changes in material structure (e.g., detection of molecular vibrations is very sensitive to changes in chemistry and structure), analyzing samples in aqueous solutions (e.g., suspensions, biological samples, etc.), and the like.

Figure 2:
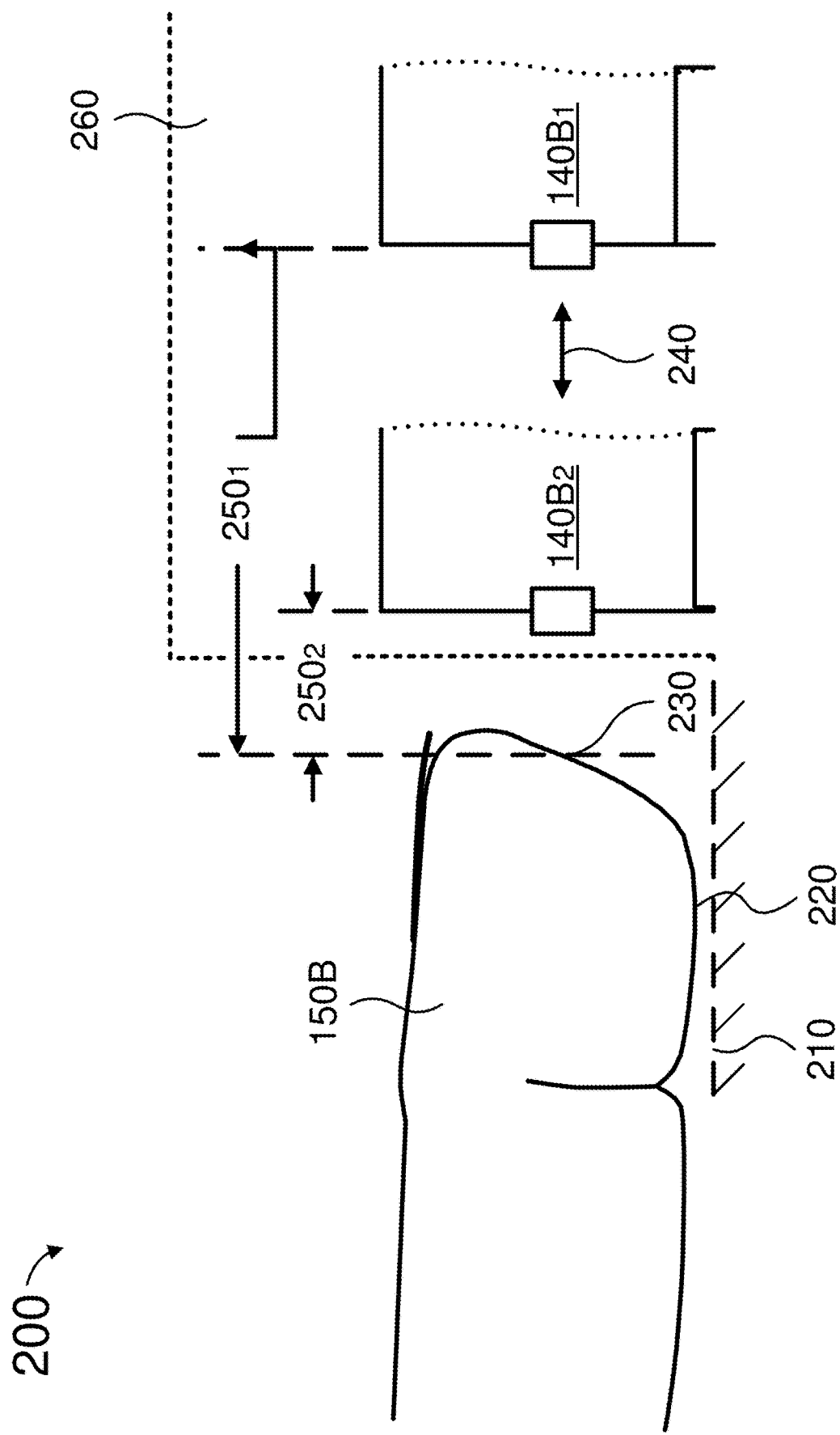
FIG. 2 is an alternate view of a system for spatial optimization for measuring biological analytes, according to various embodiments.

FIG. 2 is a simplified representation of system 200 for spatial optimization of biological analyte measurements, according to various embodiments. System 200 includes sampling apparatus 140B and analyte 150B. Sampling apparatus 140B can have at least some of the characteristics of sampling apparatus 140A. Sampling apparatus $140B_1$ and sampling apparatus $140B_2$ are collectively referred to as sampling apparatus 140B. Sampling apparatus $140B_1$ and sampling apparatus $140B_2$ illustrate motion or different spatial positions of sampling apparatus 140B along axis 240, for example, using translation stage 146 and stepper motor 142 (FIG. 1).

Analyte 150B has at least some of the characteristics of analyte 150A (FIG. 1). Sampling apparatus 140B is depicted as being directed to a surface 230 of analyte 150B purely for illustrative purposes. In some embodiments, sampling apparatus 140B can be oriented toward other surfaces of analyte 150B, such as surface 220. Moreover, analyte 150B is depicted as a (human) finger purely for illustrative purposes. Other plant or animal tissue can be used. Alternatively or additionally, other parts of a human body (e.g., including a blood vessel, such as an earlobe, neck, face, back, chest, arm, leg, toe, and the like) may be used.

System 200 can optionally include surface 210. In some embodiments, surface 210 is a surface on which analyte 150B is placed so that analyte 150B is positioned for measurement by sampling apparatus 140B and/or analyte 150B does not substantially move during operation of system 200 (e.g., substantial movement would cause a sample to change between measurements).

During operation, sampling apparatus 140B can move along axis 240 relative to analyte 150B, such as by using translation stage 146 and stepper motor 142 (FIG. 1). For example, starting at distance $250_1$ sampling apparatus 140B (depicted by sampling apparatus $140B_1$) moves along axis 240 to distance $250_2$ (depicted by sampling apparatus $140B_2$). Alternatively or additionally, starting at distance $250_2$ sampling apparatus 140B (depicted by sampling apparatus $140B_2$) moves along axis 240 to distance $250_1$ (depicted by sampling apparatus $140B_1$).

Positions before, in-between, and after those represented by sampling apparatus $140B_1$ and sampling apparatus $140B_2$ can additionally or alternatively be used. In other words, distances greater than, in-between, and less than those represented by distance $250_1$ and distance $250_2$ can additionally or alternatively be used. According to some embodiments, sampling apparatus 140B moves in steps/increments ranging from 10 μm to 50 μm.

In various embodiments, sampling apparatus 140B is (optionally) inside enclosure 260. All or some of spectrometer 110 and computing system 190 can also be inside enclosure 260.

Figure 3:
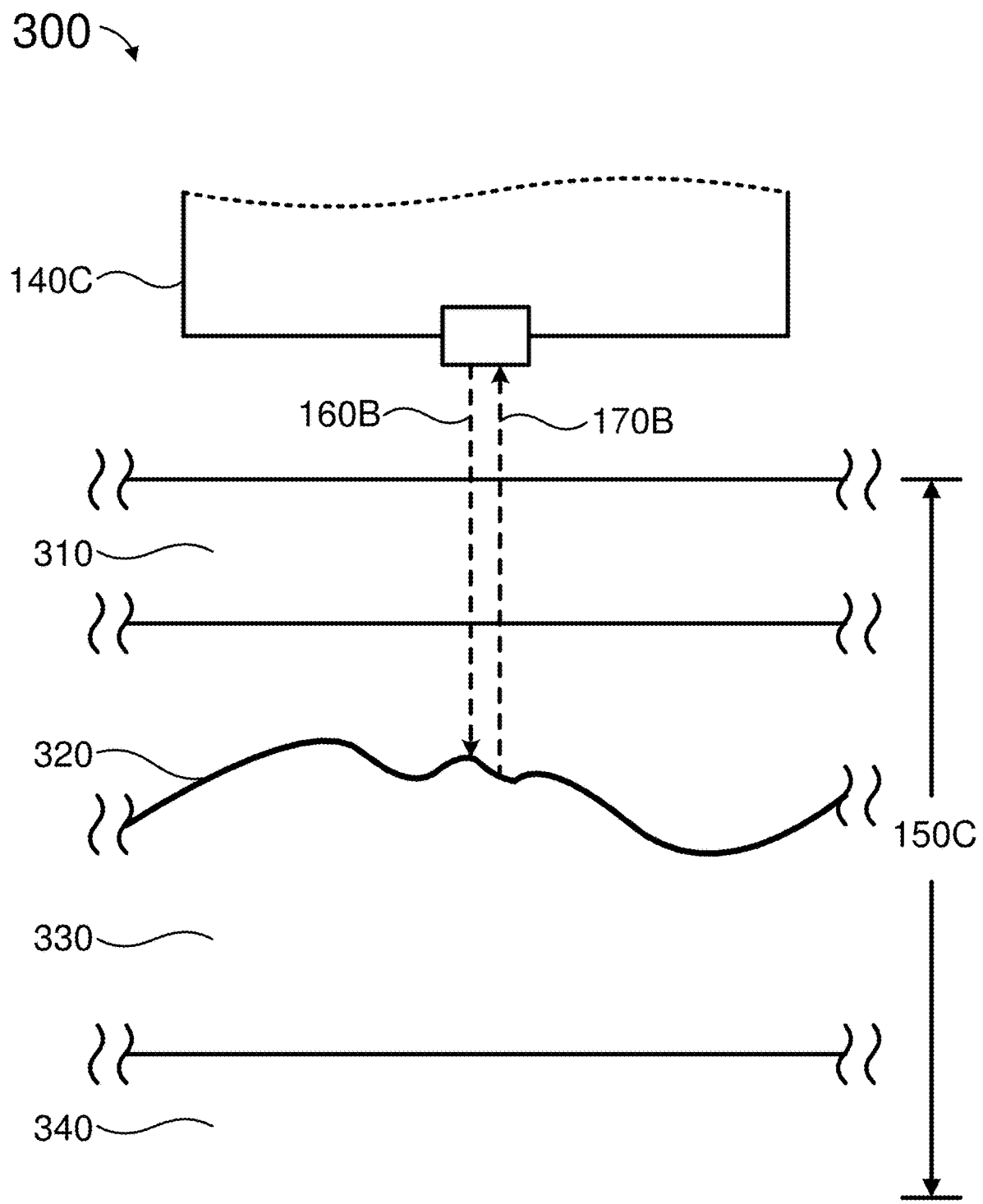
FIG. 3 is a cross-sectional view of the system of FIG. 2, in accordance with some embodiments.

FIG. 3 shows system 300, which is a simplified cross-sectional view of system 200 (FIG. 2) for spatial optimization of biological analyte measurements, in accordance with some embodiments. System 300 includes sampling apparatus 140C and analyte 150C. Sampling apparatus 140C has at least some of the characteristics of sampling apparatus 140A (FIG. 1) and sampling apparatus 140B (FIG. 2). Analyte 150C has at least some of the characteristics of analyte 150A (FIG. 1) and analyte 150B (FIG. 2).

Analyte 150C can include layers, such as epidermis 310, dermis 330, and subcutaneous (fatty) tissue 340. Dermis 330 includes blood vessel 320 (e.g., vein and/or artery). For pictorial clarity, some features of epidermis 310, dermis 330, and subcutaneous (fatty) tissue 340 (e.g., hair shaft, sweat pore and duct, sensory nerve ending, sebaceous gland, pressure sensor, hair follicle, stratum, and the like) are not shown in FIG. 3.

Light 160B can have at least some of the characteristics of light 160A (FIG. 1). Light 160B (e.g., from excitation light source 120 (FIG. 1)) illuminates analyte 150C. Light 160B can pass through epidermis 310 to dermis 330. Photons of light 160B can bounce off molecules inside blood vessel 320. (Resulting) Raman scatter (among others) 170B is received by detector 136 (FIG. 1). Raman scatter (among others) 170B can have at least some of the characteristics of Raman scatter (among others) 170A (FIG. 1).

An optimal location for taking blood measurements is where the blood is, for example, blood vessel 320. Measurement accuracy can be compromised when light 160B overshoots or undershoots blood vessel 320. In human beings, blood vessel 320 is on the order of 80 µm thick and epidermis 310 is on the order of 200 µm, so it is easy to overshoot and/or undershoot blood vessel 320 (e.g., misses blood vessel 320). Sampling apparatus 140C should be precisely positioned relative to blood vessel 320, to ensure light 160B bounces off of blood vessel 320 and a quality measurement can be taken. The proper distance from sampling apparatus 140C to blood vessel 320 to ensure accurate blood measurement can vary, though. For example, the thickness of epidermis 310 can vary depending on where it is on the body. In addition, the thickness of epidermis 310 varies from person to person. Accordingly, embodiments of the present invention advantageously move sampling apparatus 140 to an optimal position for taking spectrographic measurements.

Details of analyte 150C, such as epidermis 310, dermis 330, and subcutaneous (fatty) tissue 340, are provided purely by way of example and not limitation. Analyte 150C can include other, more, and/or fewer details than those illustrated in FIG. 3. Analyte 150C is depicted as (human) tissue purely for illustrative purposes and other plant or animal tissue can be used.

Figure 4A:
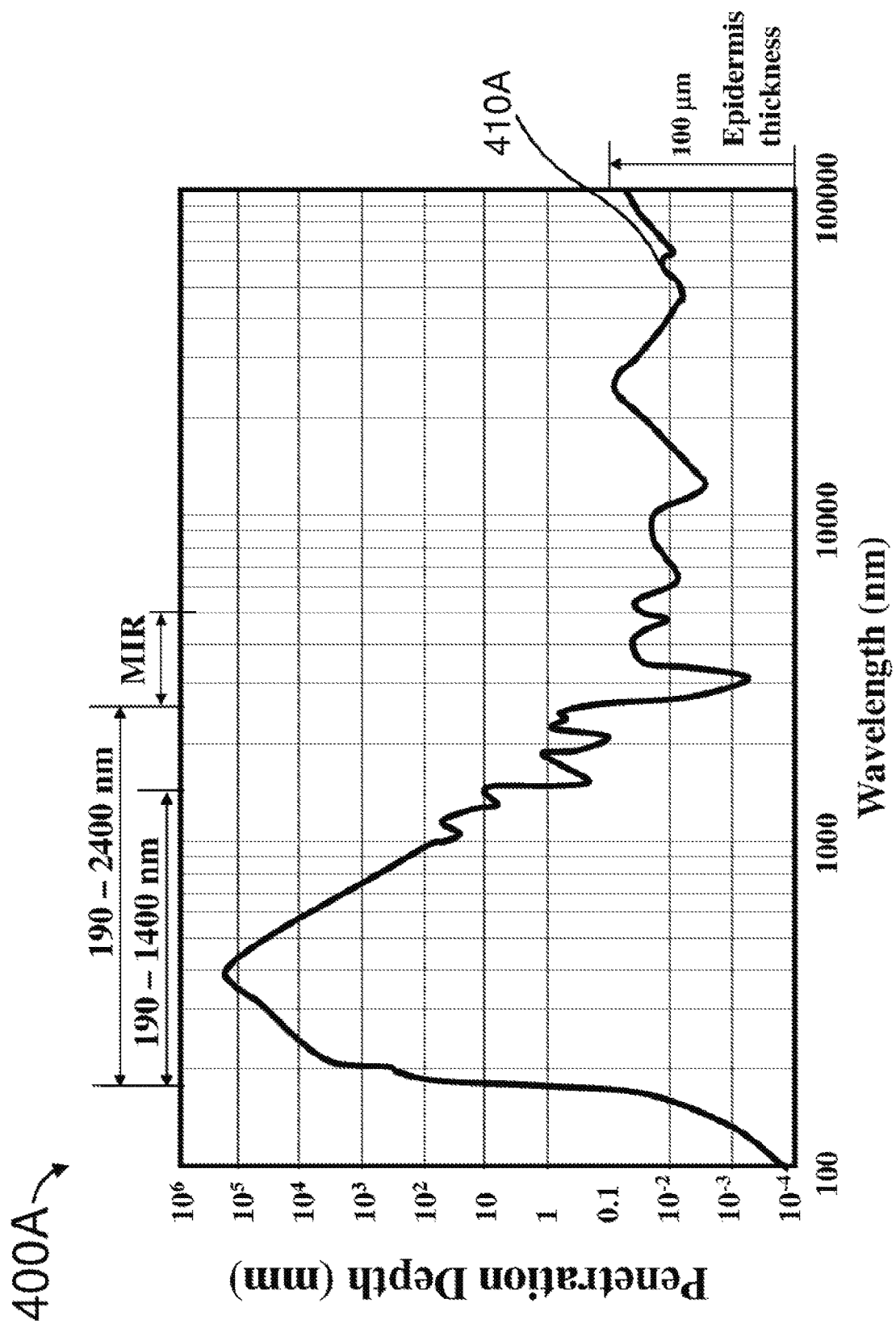
FIGS. 4A and 4B are graphical representations of penetration depth into liquid water and absorption spectra of biological tissues, respectively, in accordance with various embodiments.

FIG. 4A is a graphical representation (e.g., plot, graph, and the like) 400A of penetration depth 410A into liquid water of light over excitation wavelength. By way of non-limiting example, an epidermis (e.g., epidermis 310 in FIG. 3) can have a thickness on the order of 100 µm, so an excitation wavelength of light (e.g., light 160A and light 160B in FIGS. 1 and 3, respectfully) can be advantageously selected such that a penetration depth is at least 100 µm (e.g., approximately 190 nm to 2400 nm). In some embodiments, the excitation wavelength of light is in a range of 670 nm-900 nm for (human) tissue. Other ranges for the excitation wavelength of light can be used (e.g., depending on the depth of the tissue to be studied).

Figure 4B:
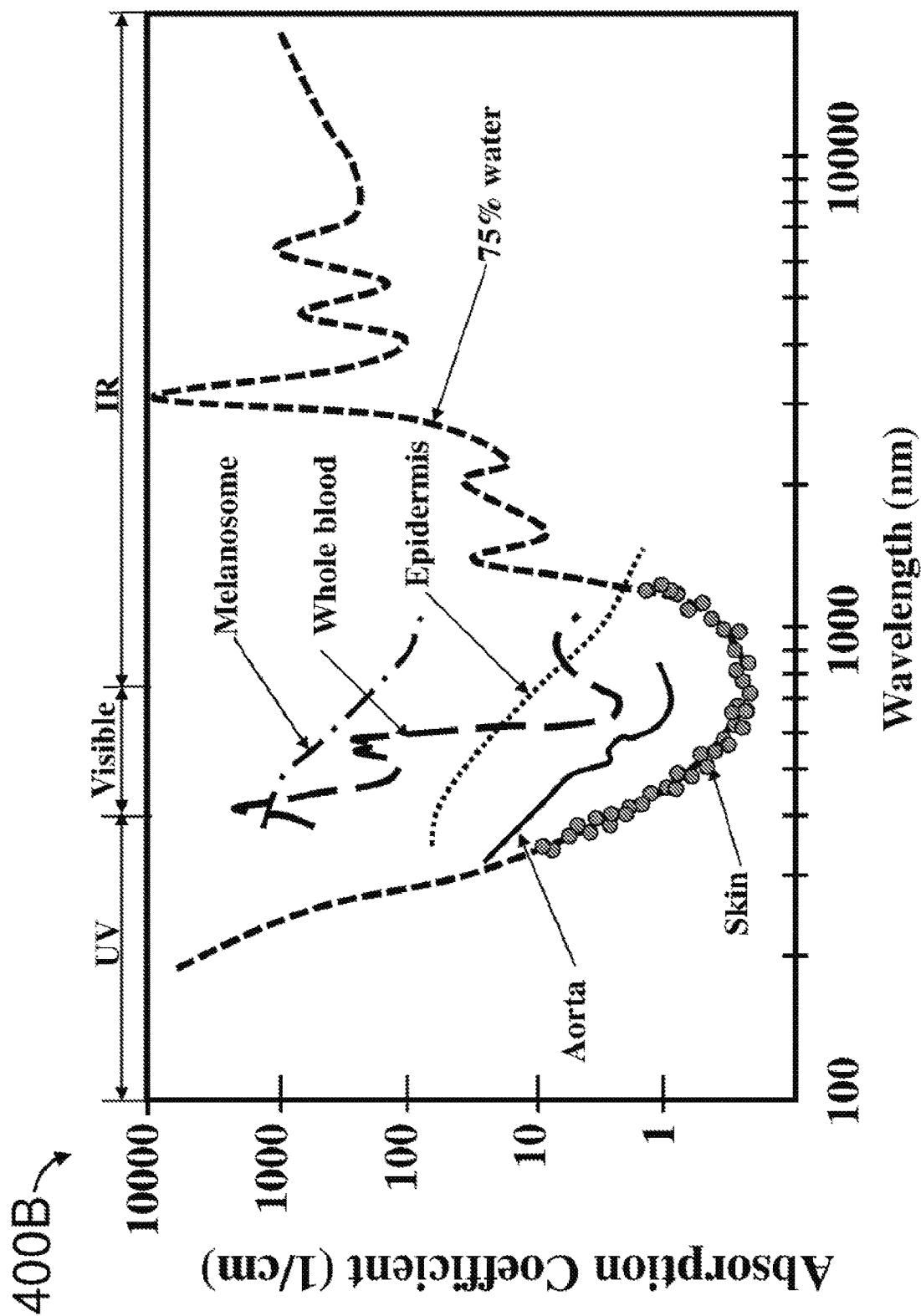

FIG. 4B is a graphical representation (e.g., plot, graph, and the like) 400B of absorption spectra of various tissues over excitation wavelength. By way of non-limiting example, an excitation wavelength of light (e.g., light 160A and light 160B in FIGS. 1 and 3, respectfully) can be advantageously selected to minimize the absorption coefficient so as to minimize absorption of the light by the tissue to be studied (e.g., so the light can scatter and be detected). When the tissue substantially absorbs light and/or Raman scatter (among others) (e.g., 170A and 170B in FIGS. 1 and 3, respectively), there can be insufficient Raman electromagnetic radiation for detector 136 to detect. For example, in skin tissue that has highly fluorescent chromophores, the increased absorption amplifies the emitted fluorescence and masks the weaker Raman signal. In various embodiments, the excitation wavelength of light is in a range of 670 nm-900 nm for (human) tissue. Other ranges for the excitation wavelength of light can be used (e.g., depending on the absorption coefficient of the tissue to be studied).

In embodiments where analyte (e.g., 150A-C (FIGS. 1-3)) is a live (and not dead) animal (e.g., living, alive, etc.), blood flows through blood vessel 320 (FIG. 3). Blood flow through blood vessel 320 in animals (e.g., humans) is caused by a heart (not shown in FIG. 4) pumping blood (e.g., beating heart). When measurements are taken at a rate slower than blood flows, different samples of blood are measured instead of the same sample and fluorescence will change with each sample.

When Raman instrument 110C takes multiple measurements, the measurements can be taken before the molecules in blood illuminated in one measurement (e.g., blood sample) flow away and are not available for the next measurement. For example, a resting adult human heart can beat at approximately 60 to 100 beats a minute (~1 Hz). Raman instrument 110C can take measurements within a tenth of a second (~0.1 kHz) or less, such that measurements are taken faster than blood flows (e.g., multiple measurements are taken from the same (instead of different) sample). Slower and/or faster sampling rates (e.g., frequency at which measurements are taken) can be used depending on the heart rate associated with analyte 150C (FIG. 3). In various embodiments, the sampling rate is 10 Hz-1 kHz.

Figure 5:
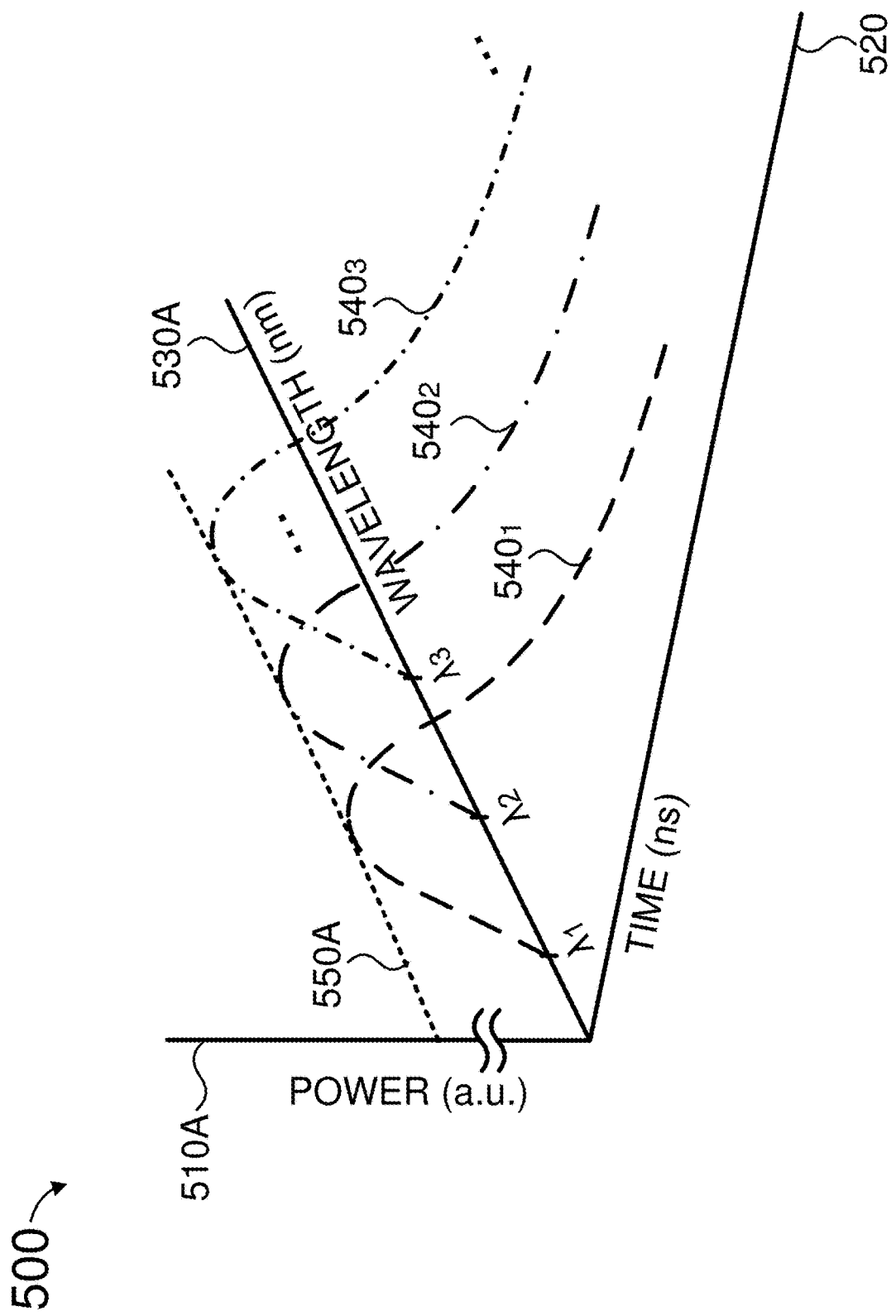
FIG. 5 is a simplified representation of spectra, according to various embodiments.

FIG. 5 illustrates example spectrum 500 produced using system 100 (FIG. 1), system 200 (FIG. 2), system 300 (FIG. 3), in some embodiments. A Raman spectrum—a plot/graph of an intensity of the Raman scattering (shifted light) against frequency—can be produced by a computing system 190 using intensity measurements from optical bench 130 (FIG. 1). Spectrum 500 (and 550A) can reliably be used to identify molecules in analyte 150A (FIG. 1), analyte 150B (FIG. 2), and analyte 150C (FIG. 3). In this way, Raman spectra (e.g., spectra 550A) can be said to produce a "fingerprint" of molecules in analyte 150. For example, Raman spectra (e.g., spectra 550A) of analyte 150 can be compared to a database (e.g., in the same or another computing system) of Raman spectra associated with known molecules to identify and quantify molecules in analyte 150A (FIG. 1), analyte 150B (FIG. 2), and analyte 150C (FIG. 3).

Spectrum 500 are plotted/graphed along three axis: intensity 510A, time 520A, and wavelength λ (or wavenumber) 530A. As shown in FIG. 5, intensity (axis 510A) can be power (light intensity) in a.u. (arbitrary units of intensity); other units can be milliwatts (mW) or photon count. Time (axis 520A) can be in nanoseconds (ns). Wavelength (axis 530A) can be a Raman shift in units such as nanometers (nm) or as a wavenumber in cm$^{-1}$. System 100 (FIG. 1), system 200 (FIG. 2), and system 300 (FIG. 3) can measure an intensity of Raman scatter having wavelength λ. For example, measurements taken at three wavelengths $\lambda_1$, $\lambda_2$, and $\lambda_3$ result in measurements 540$_1$, 540$_2$, and 540$_3$, respectively. Measurements 540$_1$, 540$_2$, and 540$_3$ show an intensity of Raman scattered light (the light having a particular wavelength $\lambda_1$, $\lambda_2$, and $\lambda_3$) over time. Measurements 540$_1$-540$_3$ can be collectively viewed when plotted/graphed along two axis: intensity 510A and wavelength λ (or wavenumber) 530A, which results in spectrum 550A (which can be referred to as a Raman spectrum). Spectrum 550A shows the peak intensity of Raman scatter at a range of wavelengths λ, such as wavelengths $\lambda_1$, $\lambda_2$, and $\lambda_3$ (or wavenumber).

Figure 6:
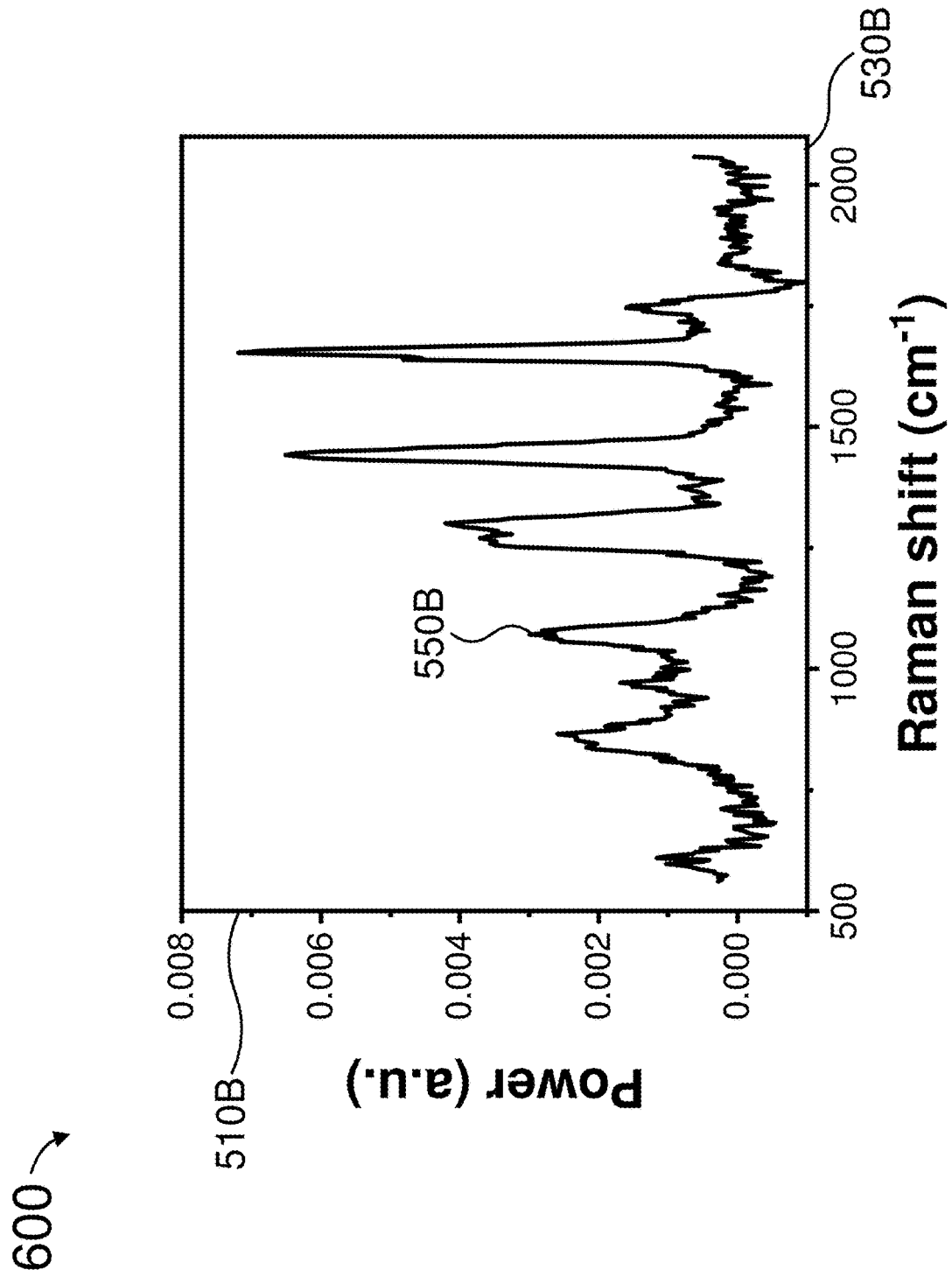
FIG. 6 is a simplified representation of a spectrum, according to some embodiments.

FIG. 6 illustrates graphical representation (e.g., plot, graph, and the like) 600 of (relative) (received) light intensity or power (e.g., in arbitrary units of intensity (a.u.), in milliwatts (mW), or photon count) along axis 510B over wavelength (e.g., in nm) (or wavenumber in cm$^{-1}$) along axis 530B, in accordance with some embodiments. Graphical representation 600 includes spectrum 550B. Spectrum 550B can have at least some of the characteristics described above for spectrum 550A (FIG. 5)

Figure 7:
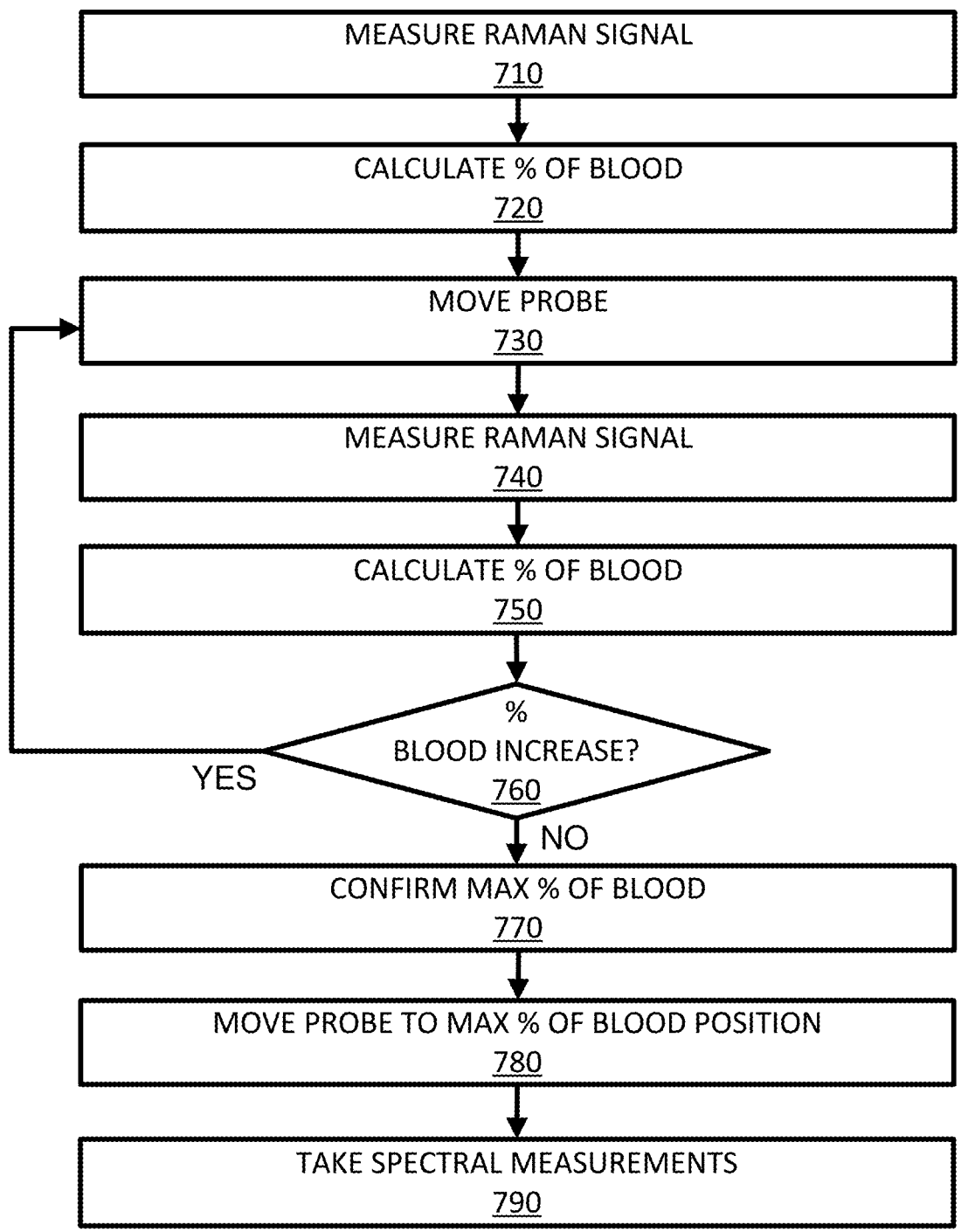
FIG. 7 is a simplified flow diagram of a method for spatial optimization, in accordance with some embodiments.

FIG. 7 illustrates method 700 for spatial optimization for measuring biological analytes, according to some embodiments. Steps of method 700 can be performed variously by system 100 (FIG. 1), system 200 (FIG. 2), and system 300 (FIG. 3). Method 700 can commence at step 710, where a Raman signal can be measured. For example, an analyte (e.g., analyte 150A (FIG. 1), analyte 150B (FIG. 2), and analyte 150C (FIG. 3)) can be illuminated (e.g., by light 160A and light 160B) and an intensity of Raman scatter (e.g., Raman scatter 170A and Raman scatter 170B) over a range of wavelengths can be measured. A non-limiting example of measurements taken at step 710 can be graphically represented as shown in and described in relation to FIGS. 5 and 6. In some embodiments, measuring the Raman signal includes taking an average 2-20 measurements and using the average at step 720. Optionally at step 710, the probe can start at a predetermined and reproducible starting position.

At step 720, a percentage of (a) blood (component) in the measured Raman signal can be determined. For example, the normalized total Raman spectrum ($\hat{S}_T$) where $$\hat{S}_T = \frac{S_T}{\max(S_T)}$$

can be modeled as a sum of signals (spectrum) of the components of tissue encountered:

$$\hat{S}_T = n_1\hat{s}_1 + n_2\hat{s}_2 + \ldots + n_k\hat{s}_k + n_b\hat{s}_b \tag{1}$$

where each component has a distinct spectrum by which the component can be identified. A spectrum for each component can be measured in advance and used to identify the component. Blood can be one of the components ($\hat{s}_b$). Other components can include keratin, melanocytes, and the like. Additional components are provided in Table 1.

TABLE 1

| COMPONENT |
| --- |
| Collagen (Type I and Type IV are in particular abundance in skin) |
| Glucose |

TABLE 1-continued

| COMPONENT |
| --- |
| Hemoglobin |
| Elastin |
| Keratin |
| Cells |
| Triolein |
| Ceramide |
| Melanin |
| Water |

Using the model of Equation 1, each component as a percentage of the total Raman signal ($\hat{S}_T$) can be determined using minimization techniques:

$$\min_n \|\hat{S}_T - (n_1\hat{s}_1 + n_2\hat{s}_2 + \ldots + n_k\hat{s}_k + n_b\hat{s}_b)\|_2^2 \tag{2}$$

A constraint to the system—each n being between 0 and 1—is shown in Equation (3).

$$s.t. \; 0 \leq n_k \leq 1 \tag{3}$$

In some embodiments, another constraint can be that the portion of each component can be safely assumed to sum to unity, as depicted in Equation (4).

$$\sum_{i=1}^{k} n_i = 1 \tag{4}$$

For example, where all the components present in an analyte (e.g., analyte 150A (FIG. 1), analyte 150B (FIG. 2), and analyte 150C (FIG. 3)) are not included in the model, the portions of components included in the model sum to 1 with some margin and the portion of omitted components is negligible (e.g., less than 0.001). In other words, the total of the portions of the omitted components can be less than 0.001. By way of non-limiting example, minimization techniques can include the Trust Region Reflective Algorithm, Steepest Descent Algorithm, Simplex Method, Sequential Least Squares Programming (SLSQP), and the like. In this way, the amount of blood as percentage of the total Raman signal ($\hat{S}_T$) can be determined.

At step 730, a probe (e.g., sampling apparatus 140A (FIG. 1), 140B (FIG. 2), and 140C (FIG. 3)) can be moved. For example, the probe can be on a translation stage (e.g., translation stage 146) and moved along an axis (e.g., axis 240) using a stepper motor (e.g., stepper motor 142). Additionally, a rotational position of the stepper motor (and/or position of the probe) can be stored (e.g., by computing system 190), so that the probe can subsequently return to this position. According to some embodiments, the probe is moved a predefined distance in a range from 10 μm to 50 μm.

At step 740, a Raman signal can be measured. In various embodiments, the Raman signal is measured such as described for step 710 (except the average of measurements is used at step 750). At step 750, a percentage of (a) blood (component) in the measured Raman signal can be determined. According to some embodiments, the percentage of blood in the measured Raman signal can be determined such as described for step 720.

At step 760, the percentage of (the) blood (component) calculated at step 750 (current calculated percentage) is compared to the percentage of (the) blood (component) calculated in the immediately preceding blood (component) percentage calculation (immediately preceding calculated percentage), such as the preceding iteration of steps 730-750 or steps 710-720. In other words, when the immediately preceding calculated percentage was calculated at step 720, the value calculated at step 720 is compared to the current calculated percentage. When the immediately preceding calculated percentage was calculated at step 750, the value calculated at step 750 is compared to the current calculated percentage. When the percentage of (the) blood (component) increases (e.g., the current calculated percentage is greater than (or equal to) the immediately preceding calculated percentage) method 700 returns to step 730. When the percentage of (the) blood (component) does not increase (e.g., the current calculated percentage is less than the immediately preceding calculated percentage), method 700 proceeds to step 770.

When the percentage of (the) blood (component) does not increase, the maximum percentage of (the) blood (component) may be reached, for example, due to the probe being optimally positioned and the laser light (e.g., by light 160A (FIG. 1) and light 160B (FIG. 3)) hitting (not overshooting or undershooting) blood vessel 320. In other words, the optimal depth for blood measurements is where the proportion of (the) blood (component) in the spectrum is at its maximum. At step 770, that the maximum blood (component) percentage (and hence optimal depth) has been found is confirmed. For example, steps 730-750 can be repeated 1 to 12 more times and each time a decrease in the percentage of (the) blood (component) is checked. Should the percentage of (the) blood (component) increase, the probe can be reset to a starting position and method 700 restarted at step 710.

At step 780, the probe is moved to the position where the maximum blood (component) percentage was measured (optimal probe position). For example, stepper motor 142 (FIG. 1) can precisely move the probe back to the (stored) position where the maximum blood (component) percentage was measured.

At step 790, spectral measurements can be taken from the optimal probe position. The Raman signal measurements taken at steps 710 and 740, for example, are designed to determine a percentage of components and not absolute concentrations. The spectral measurements at step 790 may take more detailed measurements than the Raman signal measurements at steps 710 and 740. By way of non-limiting example, spectral measurements of blood can be used to detect molecules for diagnostic purposes. Examples of molecules that can be detected at step 790 are provided in Table 2.

TABLE 2

| MOLECULE | DIAGNOSTIC FOR |
|---|---|
| Carotenoid | Antioxidant levels |
| Glucose (HbA1c test) | Diabetes |
| Colon cancer biomarker (BM) | Cancer |
| Liver cancer BM | Cancer |
| Lung cancer BM | Cancer |
| Melanoma BM | Cancer |
| Stomach cancer BM | Cancer |
| HDL Cholesterol | Heart Disease |
| LDL Cholesterol | Heart Disease |
| Triglycerides | Heart Disease |

Blood is used for illustrative purposes only and other components can be spatially optimized for and the presence (or absence or concentrations) of different molecules detected.

Figure 8:
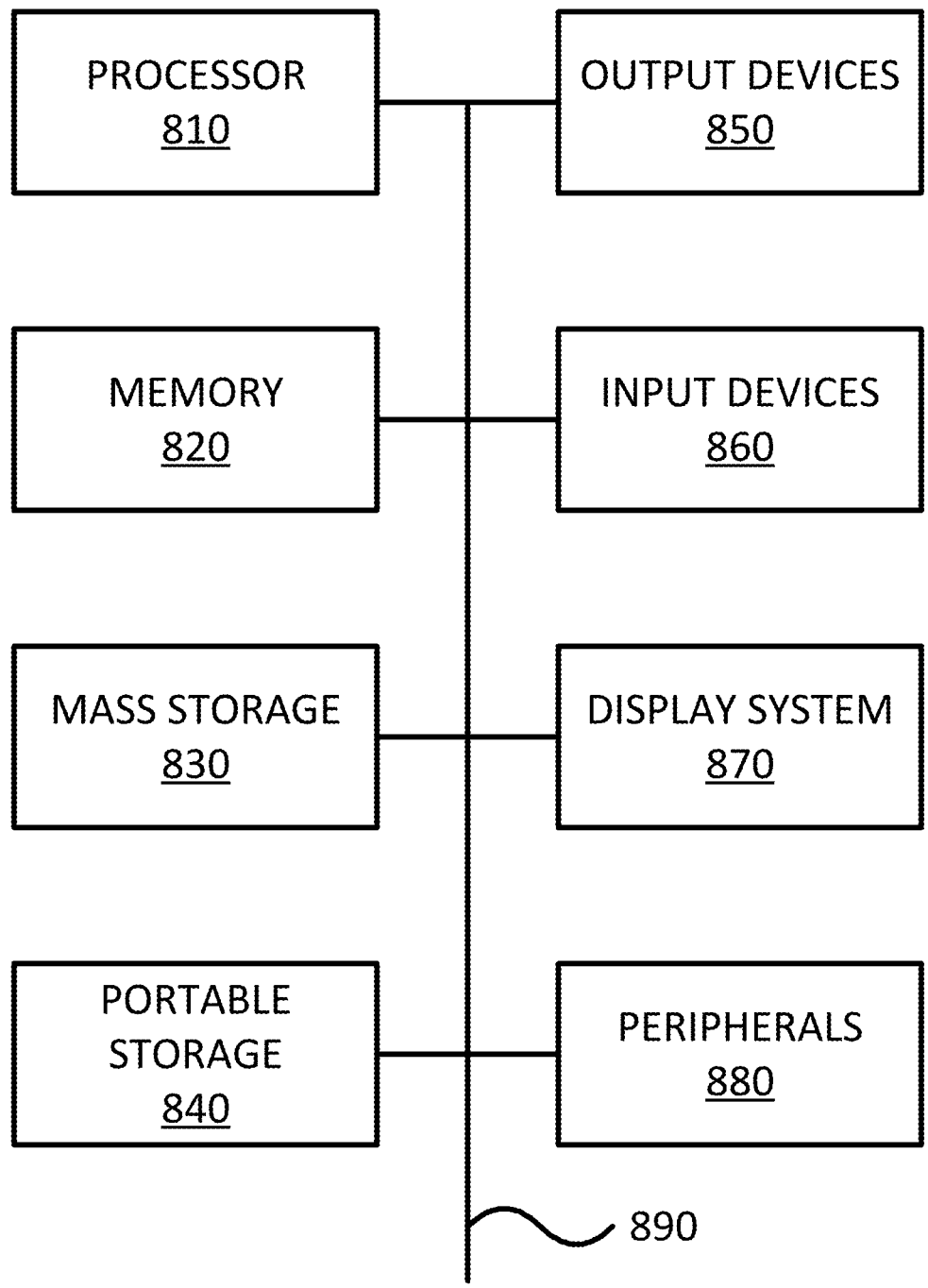
FIG. 8 is a simplified block diagram of a computing system, according to various embodiments.

FIG. 8 illustrates an exemplary computer system 800 that may be used to implement some embodiments of the present invention. The computer system 800 in FIG. 8 may be implemented in the contexts of the likes of computing systems, networks, servers, or combinations thereof. The computer system 800 in FIG. 8 includes one or more processor unit(s) 810 and main memory 820. Main memory 820 stores, in part, instructions and data for execution by processor unit(s) 810. Main memory 820 stores the executable code when in operation, in this example. The computer system 800 in FIG. 8 further includes a mass data storage 830, portable storage device 840, output devices 850, user input devices 860, a graphics display system 870, and peripheral device(s) 880.

The components shown in FIG. 8 are depicted as being connected via a single bus 890. The components may be connected through one or more data transport means. Processor unit(s) 810 and main memory 820 are connected via a local microprocessor bus, and the mass data storage 830, peripheral device(s) 880, portable storage device 840, and graphics display system 870 are connected via one or more input/output (I/O) buses.

Mass data storage 830, which can be implemented with a magnetic disk drive, solid state drive, or an optical disk drive, is a non-volatile storage device for storing data and instructions for use by processor unit(s) 810. Mass data storage 830 stores the system software for implementing embodiments of the present disclosure for purposes of loading that software into main memory 820.

Portable storage device 840 operates in conjunction with a portable non-volatile storage medium, such as a flash drive, floppy disk, compact disk, digital video disc, or Universal Serial Bus (USB) storage device, to input and output data and code to and from the computer system 800 in FIG. 8. The system software for implementing embodiments of the present disclosure is stored on such a portable medium and input to the computer system 800 via the portable storage device 840.

User input devices 860 can provide a portion of a user interface. User input devices 860 may include one or more microphones, an alphanumeric keypad, such as a keyboard, for inputting alphanumeric and other information, or a pointing device, such as a mouse, a trackball, stylus, or cursor direction keys. User input devices 860 can also include a touchscreen. Additionally, the computer system 800 as shown in FIG. 8 includes output devices 850. Suitable output devices 850 include speakers, printers, network interfaces, and monitors.

Graphics display system 870 include a liquid crystal display (LCD) or other suitable display device. Graphics display system 870 is configurable to receive textual and graphical information and processes the information for output to the display device.

Peripheral device(s) 880 may include any type of computer support device to add additional functionality to the computer system.

The components provided in the computer system 800 in FIG. 8 are those typically found in computer systems that may be suitable for use with embodiments of the present disclosure and are intended to represent a broad category of such computer components that are well known in the art. Thus, the computer system 800 in FIG. 8 can be a personal computer (PC), hand held computer system, telephone, mobile computer system, workstation, tablet, phablet, mobile phone, server, minicomputer, mainframe computer, wearable, or any other computer system. The computer may also include different bus configurations, networked platforms, multi-processor platforms, and the like. Various operating systems may be used including UNIX, LINUX, WIN- DOWS, MAC OS, PALM OS, QNX, ANDROID, IOS, CHROME, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the technology. Those skilled in the art are familiar with instructions, processor(s), and storage media.

In some embodiments, the computing system 800 may be implemented as a cloud-based computing environment, such as a virtual machine operating within a computing cloud. In other embodiments, the computing system 800 may itself include a cloud-based computing environment, where the functionalities of the computing system 800 are executed in a distributed fashion. Thus, the computing system 800, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud is formed, for example, by a network of web servers that comprise a plurality of computing devices, such as the computing system 800, with each server (or at least a plurality thereof) providing processor and/or storage resources. These servers manage workloads provided by multiple users (e.g., cloud resource customers or other users). Typically, each user places workload demands upon the cloud that vary in real-time, sometimes dramatically. The nature and extent of these variations typically depends on the type of business associated with the user.

It is noteworthy that any hardware platform suitable for performing the processing described herein is suitable for use with the technology. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical, magnetic, and solid-state disks, such as a fixed disk. Volatile media include dynamic memory, such as system random-access memory (RAM). Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic medium, a CD-ROM disk, digital video disk (DVD), any other optical medium, any other physical medium with patterns of marks or holes, a RAM, a programmable read-only memory (PROM), an erasable programmable read-only memory (EPROM), an electrically erasable programmable read-only memory (EEPROM), a Flash memory, any other memory chip or data exchange adapter, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Computer program code for carrying out operations for aspects of the present technology may be written in any combination of one or more programming languages, including an object oriented programming language such as JAVA, SMALLTALK, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of wired and/or wireless network, including a (wireless) local area network (LAN/WLAN) or a (wireless) wide area network (WAN/WWAN), or the connection may be made to an external computer (for example, through the Internet using an Internet Service Provider, wireless Internet provider, and the like).

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated. The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

What is claimed is:

1. A method for spatial optimization of blood measurements in tissue, the method comprising:
   measuring a first Raman signal from the tissue with a probe at a first position;
   calculating a first percentage of a blood component in the first Raman signal;

moving the probe a predetermined distance to a second position;
measuring a second Raman signal from the tissue with the probe at the second position;
calculating a second percentage of the blood component in the second Raman signal;
moving the probe a predetermined distance to a third position when the second percentage is greater than the first percentage;
measuring a third Raman signal from the tissue with the probe at the third position;
calculating a third percentage of the blood component in the third Raman signal;
moving the probe to the second position when the third percentage is less than the second percentage; and
taking spectral measurements from the second position.

2. The method of claim 1 wherein the calculating the first percentage, the calculating the second percentage, and the calculating the third percentage comprise:
modeling each of the first Raman signal, the second Raman signal, and the third Raman signal as a sum of signals associated with a plurality of components to produce a model, the signals associated with the plurality of components being previously measured, the plurality of components including a blood component; and
applying a minimization technique to each model of the first Raman signal, the second Raman signal, and the third Raman signal to determine the first percentage, the second percentage, and the third percentage.

3. The method of claim 2, wherein the minimization technique is a Trusted Region Reflective Algorithm.

4. The method of claim 1 wherein the measuring the first Raman signal, the measuring the second Raman signal, and the measuring the third Raman signal comprise:
providing a first light using an excitation light source; and
receiving, by a detector, scattered light from the tissue responsive to the first light.

5. The method of claim 4, wherein the excitation light source is a laser having power in a range from 100 mW to 250 mW.

6. The method of claim 4, wherein the measuring the first Raman signal, the measuring the second Raman signal, and the measuring the third Raman signal further comprise:
taking an average of a number of iterations of receiving, by the detector, the scattered light from the tissue responsive to the first light, the number of iterations being in a range from 2 to 20; and
using the average as a respective one of the first Raman signal, the second Raman signal, and the third Raman signal.

7. The method of claim 1, wherein the predetermined distance is in a range from 10 μm to 50 μm.

8. The method of claim 1, wherein the moving the probe to the second position and the moving the probe to the third position is along an axis.

9. The method of claim 8, wherein the probe moves along the axis using a translation stage.

10. The method of claim 9, wherein the translation stage moves using a stepper motor.

11. A system for spatial optimization of blood measurements in tissue, the system comprising:
a processor; and
a memory, the memory communicatively coupled to the processor and storing instructions executable by the processor to perform a method, the method comprising:
measuring a first Raman signal from the tissue with a probe at a first position;
calculating a first percentage of a blood component in the first Raman signal;
moving the probe a predetermined distance to a second position;
measuring a second Raman signal from the tissue with the probe at the second position;
calculating a second percentage of the blood component in the second Raman signal;
moving the probe a predetermined distance to a third position when the second percentage is greater than the first percentage;
measuring a third Raman signal from the tissue with the probe at the third position;
calculating a third percentage of the blood component in the third Raman signal;
moving the probe to the second position when the third percentage is less than the second percentage; and
taking spectral measurements from the second position.

12. The system of claim 11, wherein the calculating the first percentage, the calculating the second percentage, and the calculating the third percentage comprise:
modeling each of the first Raman signal, the second Raman signal, and the third Raman signal as a sum of signals associated with a plurality of components to produce a model, the signals associated with the plurality of components being previously measured, the plurality of components including a blood component; and
applying a minimization technique to each model of the first Raman signal, the second Raman signal, and the third Raman signal to determine the first percentage, the second percentage, and the third percentage.

13. The system of claim 12, wherein the minimization technique is a Trusted Region Reflective Algorithm.

14. The system of claim 11, wherein the measuring the first Raman signal, the measuring the second Raman signal, and the measuring the third Raman signal comprise:
providing a first light using an excitation light source; and
receiving, by a detector, scattered light from the tissue responsive to the first light.

15. The system of claim 14, wherein the excitation light source is a laser having power in a range from 100 mW to 250 mW.

16. The system of claim 14, wherein the measuring the first Raman signal, the measuring the second Raman signal, and the measuring the third Raman signal further comprise:
taking an average of a number of iterations of receiving, by the detector, the scattered light from the tissue responsive to the first light, the number of iterations being in a range from 2 to 20; and
using the average as a respective one of the first Raman signal, the second Raman signal, and the third Raman signal.

17. The system of claim 11, wherein the predetermined distance is in a range from 10 μm to 50 μm.

18. The system of claim 11, wherein the moving the probe to the second position and the moving the probe to the third position is along an axis.

19. The system of claim 18, wherein:
the probe moves along the axis using a translation stage, and
the translation stage moves using a stepper motor.

20. A system for spatial optimization of blood measurements in tissue, the system comprising:

means for measuring a first Raman signal from the tissue with a probe at a first position;
means for calculating a first percentage of a blood component in the first Raman signal;
means for moving the probe a predetermined distance to a second position;
means for measuring a second Raman signal from the tissue with the probe at the second position;
means for calculating a second percentage of the blood component in the second Raman signal;
means for moving the probe a predetermined distance to a third position when the second percentage is greater than the first percentage;
means for measuring a third Raman signal from the tissue with the probe at the third position;
means for calculating a third percentage of the blood component in the third Raman signal;
means for moving the probe to the second position when the third percentage is less than the second percentage; and
means for taking spectral measurements from the second position.

* * * * *